US008684992B2

(12) United States Patent
Sullivan et al.

(10) Patent No.: US 8,684,992 B2
(45) **Date of Patent: *Apr. 1, 2014**

(54) VIAL ADAPTOR

(75) Inventors: Roy H. Sullivan, Millville, MA (US); Katie L. Krueger, Merrimack, NH (US); Joseph A. Levendusky, Groton, MA (US); Timothy C. Wech, Roslindale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 474 days.

This patent is subject to a terminal disclaimer.

(21) Appl. No.: 12/586,569

(22) Filed: Sep. 24, 2009

(65) Prior Publication Data

US 2010/0022985 A1 Jan. 28, 2010

Related U.S. Application Data

(63) Continuation of application No. 10/909,692, filed on Jul. 29, 2004, now Pat. No. 7,615,041.

(51) Int. Cl.
*A61B 19/00* (2006.01)

(52) U.S. Cl.
USPC .......................................... 604/411; 604/403

(58) Field of Classification Search
USPC ............... 604/30, 33, 34, 36, 167.01–167.06, 604/403–416; 215/247
See application file for complete search history.

(56) References Cited

U.S. PATENT DOCUMENTS 2,771,074 A 11/1956 Landsperger et al.
4,128,098 A 12/1978 Bloom et al.
(Continued)

FOREIGN PATENT DOCUMENTS

FR 2828803 A1 2/2003
WO 97/20536 A1 6/1997
(Continued)

OTHER PUBLICATIONS

International Search Report for PCT Appln. No. PCT/US2005/027306, mailed Dec. 5, 2005.
(Continued)

*Primary Examiner* — Philip R Wiest
(74) *Attorney, Agent, or Firm* — Mayer & Williams PC; David B. Bonham

(57) ABSTRACT

A vial adapter suitable for use in transferring fluid from a vial to a needleless syringe, the vial having a top end sealed with a septum. According to one embodiment, the vial adapter comprises (a) a body, the body having a top end, a bottom end and an inner cavity, the inner cavity being dimensioned to receive the vial, with the bottom end of the body extending below the bottom end of the vial; (b) a needle-bearing member mounted within the body, the needle-bearing member comprising a hollow needle extending downwardly into the inner cavity of the body for puncturing the septum of a vial disposed in the inner cavity; (c) a luer-lock-bearing member mounted on the top end of the body, the luer-lock-bearing member comprising a top portion and a bottom portion separated by a radial wall, the top portion being a female luer-lock, the bottom portion including a tubular structure in fluid communication with the hollow needle; and (d) a valve disposed within the luer-lock-bearing member for controlling fluid flow from the bottom portion to the top portion, the valve being opened by attachment of the needleless syringe to the vial adapter.

28 Claims, 15 Drawing Sheets

(56) References Cited

U.S. PATENT DOCUMENTS

| | | | | |
|---|---|---|---|---|
| 4,576,211 | A | 3/1986 | Valentini et al. | |
| 4,872,494 | A | 10/1989 | Coccia | |
| 4,982,769 | A | 1/1991 | Fournier et al. | |
| 4,994,029 | A | 2/1991 | Rohrbough | |
| 5,100,394 | A | 3/1992 | Dudar et al. | |
| 5,342,346 | A * | 8/1994 | Honda et al. | 604/413 |
| 5,411,499 | A | 5/1995 | Dudar et al. | |
| 5,423,791 | A | 6/1995 | Bartlett | |
| 5,429,256 | A | 7/1995 | Kestenbaum | |
| 5,478,337 | A * | 12/1995 | Okamoto et al. | 604/413 |
| 5,509,433 | A | 4/1996 | Paradis | |
| 5,527,306 | A | 6/1996 | Haining | |
| 5,620,427 | A | 4/1997 | Werschmidt et al. | |
| 5,620,434 | A | 4/1997 | Brony | |
| 5,667,767 | A | 9/1997 | Greff et al. | |
| 5,743,312 | A | 4/1998 | Pfeifer et al. | |
| 5,782,816 | A | 7/1998 | Werschmidt et al. | |
| 5,833,213 | A * | 11/1998 | Ryan | 251/149.1 |
| 5,846,233 | A | 12/1998 | Lilley et al. | |
| 6,003,566 | A | 12/1999 | Thibault et al. | |
| 6,050,978 | A | 4/2000 | Orr et al. | |
| 6,089,541 | A | 7/2000 | Weinheimer et al. | |
| 6,090,093 | A | 7/2000 | Thibault et al. | |
| 6,142,446 | A | 11/2000 | Leinsing | |
| 6,170,800 | B1 | 1/2001 | Meloul et al. | |
| 6,189,580 | B1 | 2/2001 | Thibault et al. | |
| 6,238,335 | B1 | 5/2001 | Silverman et al. | |
| 6,258,078 | B1 | 7/2001 | Thilly | |
| 6,293,293 | B1 | 9/2001 | Wrigley et al. | |
| 6,344,033 | B1 | 2/2002 | Jepson et al. | |
| 6,378,576 | B2 | 4/2002 | Thibault et al. | |
| 6,378,714 | B1 | 4/2002 | Jansen et al. | |
| 6,428,520 | B1 | 8/2002 | Lopez et al. | |
| 6,478,788 | B1 | 11/2002 | Aneas | |
| 6,524,295 | B2 | 2/2003 | Daubert et al. | |
| 6,527,011 | B1 | 3/2003 | Mantz | |
| 6,537,263 | B1 | 3/2003 | Aneas | |
| 6,591,876 | B2 | 7/2003 | Safabash | |
| 6,599,273 | B1 | 7/2003 | Lopez | |
| 6,601,721 | B2 | 8/2003 | Jansen et al. | |
| 6,626,309 | B1 | 9/2003 | Jansen et al. | |
| 6,656,433 | B2 | 12/2003 | Sasso | |
| 2001/0025672 | A1 | 10/2001 | Thibault et al. | |
| 2002/0079285 | A1 | 6/2002 | Jansen et al. | |
| 2002/0121496 | A1 | 9/2002 | Thiebault et al. | |
| 2002/0127150 | A1 | 9/2002 | Sasso | |
| 2002/0165504 | A1 * | 11/2002 | Sharp et al. | 604/272 |
| 2002/0189712 | A1 | 12/2002 | Safabash | |
| 2004/0186457 | A1 * | 9/2004 | Truitt et al. | 604/403 |

FOREIGN PATENT DOCUMENTS

| | | | | |
|---|---|---|---|---|
| WO | 03017916 A1 | | 3/2003 | |
| WO | WO 03/017916 | * | 3/2003 | A61J 1/20 |

OTHER PUBLICATIONS

Printout of pages from www.qosina.com showing Product No. 91022, Qosina Corp., Edgewood, NY (date unknown, but prior to the filing date of the parent application).

Printout of pages from www.amsino.com showing Product No. AY0100, Vial Adapter with AMSafe® PRN Connector, Amsino International Inc., Ontario, CA (date unknown, but prior to the filing date of the parent application).

* cited by examiner

VIAL ADAPTOR

CROSS-REFERENCE TO RELATED APPLICATIONS

The present application is a continuation of U.S. patent application Ser. No. 10/909,692, inventors Roy H. Sullivan et al., filed Jul. 29, 2004, now U.S. Pat. No. 7,615,041 the disclosure of which is herein incorporated by reference.

BACKGROUND OF THE INVENTION

The present invention relates generally to adaptors of the type that are used to fluidly interconnect a vial to a needleless syringe and relates more particularly to a novel such adaptor.

Nearly half of all Americans suffer from heartburn at least one month. Heartburn occurs when stomach fluids and acids escape from the stomach and enter into the esophagus, irritating the esophagus. Normally, a muscular ring called the lower esophageal sphincter (LES) acts as a valve between the esophagus and the stomach to allow food to pass from the esophagus into the stomach while keeping stomach fluids and acids from escaping from the stomach into the esophagus. In those instances in which the LES fails to keep stomach fluids and acids in the stomach, heartburn occurs.

For some people who suffer from heartburn, the heartburn is severe enough or frequent enough to disrupt their daily activities and/or their sleep. Such a condition is called gastroesophageal reflux disease (GERD). In some people who have GERD, the LES relaxes more than it should and/or at the wrong times.

In addition to causing frequent and/or severe heartburn, GERD can cause other health problems. For example, the fluids and acids that reflux into the esophagus can lead to inflammation of the esophagus (esophagitis) or ulcers. In severe cases, this damage can scar the esophageal lining and narrow it, causing a stricture which may make it hard or painful for the patient to swallow. In certain cases, this may lead to a condition called Barrett's esophagus, where the lining of the esophagus changes and may over time lead to cancer of the esophagus.

Many people can get relief from GERD symptoms by changing their diet and/or using appropriate medications. Some of the medications available for managing GERD symptoms include common antacids as well as drugs that slow down the production of stomach acids, such as proton pump inhibitors and $H_2$ receptor antagonists.

It should be noted, however, that medications of the type described above merely address symptoms of GERD and do not address the condition's mechanical etiology. Thus, GERD symptoms often recur after drug withdrawal. In addition, while medications may effectively treat the acid-induced symptoms of GERD, they do not treat alkaline reflux, which may result in esophageal mucosal injury.

In any event, because GERD is a chronic condition, it may be necessary for a patient to take medications for the rest of his life in order to continue to obtain relief from GERD symptoms. However, for many patients, the expense and the psychological burden of a lifetime of medication dependence, as well as the uncertainty of long-term effects of some newer medications and the potential for persistent mucosal changes despite symptomatic control, make surgical treatment an alluring alternative to a medicinal approach. As can readily be appreciated, however, surgical intervention, often in the form of anti-reflux surgery, is a major undertaking and includes its own set of risks.

Fortunately, a minimally invasive technique has recently been devised for treating GERD. This technique, which is more fully disclosed in U.S. Pat. Nos. 6,238,335, 6,251,063 and 6,351,064, all of which are incorporated herein by reference, typically involves (i) inserting an endoscope down through the patient's mouth and into the esophagus in proximity to the LES, (ii) then, inserting a catheter having a needle at its distal end down through a channel of the endoscope and into the muscle of the LES, and (iii) then, dispensing a special solution through the catheter and needle and into the muscle of the LES. The solution, which is commercially available from Boston Scientific Corporation (Natick, Mass.) as Enteryx® solution, includes a biocompatible polymer that forms a soft, spongy, permanent implant in the sphincter muscle that helps the LES to keep stomach fluids and acids from backing up into the esophagus.

Typically, the manner in which the Enteryx® solution is loaded into the catheter for injection into the patient is by withdrawing a volume of the solution from a sealed vial using a needle-bearing syringe (i.e., by inserting the tip of the needle through the septum sealing the vial and into the solution contained within the vial and then withdrawing solution from the vial through the needle and into the syringe), detaching the needle from the syringe, and then dispensing the withdrawn volume from the syringe into the catheter. This same technique is also typically used to transfer a liquid primer, typically dimethylsulfoxide (DMSO), from a sealed vial to the catheter.

As can readily be appreciated, the aforementioned use of exposed needles to transfer liquids from sealed vials to the catheter poses certain health and safety risks, such as user injury, exposure to contaminate from the needle and transmission of disease. Accordingly, care must be taken to cap the needle whenever the needle is not in use. Moreover, because the polymeric solution must be injected into the patient at a slow rate, typically requiring the use of a small-volume syringe that must be loaded a plurality of times, the aforementioned use of needles can be quite cumbersome as it is necessary for the needle to be repeatedly attached to and detached from the syringe each time the syringe is loaded with liquid.

Another problem that is posed by the above-described use of needle-bearing syringes to withdraw the polymeric solution and the liquid primer from their respective vials is that there is no way to ensure that the contents of the two vials are being used for the treatment of only one patient. In other words, because the vials typically contain more liquid than is required for one procedure, it is conceivable that the remnants of a plurality of like vials may be combined to treat one or more additional patients. This is undesirable as it may be necessary in certain instances to trace the source of the liquids being administered and/or to prevent the liquids from being used after a certain date.

Although not specifically designed for transferring the particular liquids discussed above, there do exist a number of devices that are adapted for use in transferring liquids from sealed vials to needle-less syringes. One such device is disclosed in U.S. Pat. No. 5,833,213, inventor Ryan, which issued Nov. 10, 1998, and is incorporated herein by reference. The aforementioned Ryan device is a vial adapter that includes a first coupling member having a female luer lock connector with a fluid path therethrough, a flange having a first sealing ring seat formed therein and a first mating structure; a second coupling member having a centrally located septum piercing tube with a fluid path therethrough and a second mating structure; and a valve member including a valve stem and a resilient valve body having an annular sealing surface. A valve body seat is formed in the interior of the second coupling member by a plurality of radially arranged stepped vanes. The second coupling member is formed as a stepped cylinder having a relatively large diameter adjacent the point of the septum piercing tube, a relatively small diameter adjacent the valve body seat and an intermediate diameter therebetween. The valve body is substantially frustoconical having a relatively broad end with a stepped axial bore defining the annular sealing surface. The valve stem has a stepped cylindrical portion which fits into the axial bore of the valve body and a pair of spaced apart upstanding members which extend into the female luer. The vial adapter is attached to a vial by aligning the point of the septum piercing tube with the center of the septum of the vial and by pushing the tube through the septum. As the tube passes through the septum, the neck of the vial is received by the second cylindrical coupling member. When a needleless syringe is attached to the vial adapter, the valve stem is moved towards the vial and the resilient valve body is compressed and moved away from a sealing ring, opening a fluid path from the septum piercing tube into the female luer, and thus into the needleless syringe. When the syringe is removed from the adapter, the resilient valve body expands and seals the fluid path.

Another such device is disclosed in U.S. Pat. No. 5,527,306, inventor Haining, which issued Jun. 18, 1996, and is incorporated herein by reference. The aforementioned Haining patent discloses an adapter for a medicinal vial that includes a conical spike on one end for insertion through the rubber puncture pad in the lid of a medicinal vial. The end opposite the spike is provided with a standard male luer connection and pre-slit rubber cover. The male luer connector of a syringe may be passed through the slit to withdraw liquid from the vial by action of a piston. The rubber cover keeps the end of the adapter sealed. The adapter may include a valve in the upper portion to seal the end which opens in response to the attachment of a syringe.

Examples of other devices for fluidly interconnecting a vial to a needleless syringe are disclosed in the following patents and published patent applications, all of which are incorporated herein by reference: U.S. Pat. No. 6,656,433, inventor Sasso, issued Dec. 2, 2003; U.S. Pat. No. 6,626,309, inventors Jansen et al., issued Sep. 30, 2003; U.S. Pat. No. 6,601,721, inventors Jansen et al., issued Aug. 5, 2003; U.S. Pat. No. 6,599,273, inventor Lopez, issued Jul. 29, 2003; U.S. Pat. No. 6,591,876, inventor Safabash, issued Jul. 15, 2003; U.S. Pat. No. 6,524,295, inventors Daubert et al., issued Feb. 25, 2003; U.S. Pat. No. 6,478,788, inventor Aneas, issued Nov. 12, 2002; U.S. Pat. No. 6,378,714, inventors Jansen et al., issued Apr. 30, 2002; U.S. Pat. No. 6,378,576, inventors Thibault et al., issued Apr. 30, 2002; U.S. Pat. No. 6,378,714, inventors Jansen et al., issued Apr. 30, 2002; U.S. Pat. No. 6,258,078, inventor Thilly, issued Jul. 10, 2001; U.S. Pat. No. 6,189,580, inventors Thibault et al., issued Feb. 20, 2001; U.S. Pat. No. 6,090,093, inventors Thibault et al., issued Jul. 18, 2000; U.S. Pat. No. 6,003,566, inventors Thibault et al., issued Dec. 21, 1999; U.S. Pat. No. 5,620,434, inventor Brony, issued Apr. 15, 1997; U.S. Pat. No. 5,509,433, inventor Paradis, issued Apr. 23, 1996; U.S. Pat. No. 5,429,256, inventor Kestenbaum, issued Jul. 4, 1995; U.S. Pat. No. 5,423,791, inventor Bartlett, issued Jun. 13, 1995; U.S. Pat. No. 4,872,494, inventor Coccia, issued Oct. 10, 1989; U.S. Pat. No. 4,576,211, inventors Valentini et al., issued Mar. 18, 1986; U.S. Pat. No. 2,771,074, issued Nov. 20, 1956; and U.S. Patent Application Publication No. US 2002/0121496 A1, published Sep. 5, 2002.

SUMMARY OF THE INVENTION

It is an object of the present invention to provide a novel vial adapter of the type adapted to fluidly interconnect a vial to a needleless syringe.

According to one aspect of the invention, there is provided a vial adapter for use in transferring fluid from a vial, the vial having a top end and a bottom end, the top end of the vial being sealed with a septum, said vial adapter comprising (a) a body, said body having a top end, a bottom end and an inner cavity, said inner cavity being dimensioned to receive the vial, with the bottom end of said body extending below the bottom end of the vial; and (b) a hollow piercing member extending downwardly into said inner cavity of said body for puncturing the septum of a vial disposed in said inner cavity.

According to another aspect of the invention, there is provided a vial adapter for use in transferring fluid from a vial, the vial having a top end and a bottom end, the top end of the vial being sealed with a septum, said vial adapter comprising (a) a body, said body having a top end, a bottom end and an inner cavity, said inner cavity being dimensioned to receive the vial, with the bottom end of said body extending below the bottom end of the vial; (b) a needle-bearing member mounted within said body, said needle-bearing member comprising a hollow needle extending downwardly into said inner cavity of said body for puncturing the septum of a vial disposed in said inner cavity; (c) a luer-lock-bearing member mounted on said top end of said body, said luer-lock-bearing member comprising a top portion and a bottom portion separated by a radial wall, said top portion being a female luer-lock, said bottom portion including a tubular member in fluid communication with said hollow needle; and (d) a valve disposed within said luer-lock-bearing member for controlling fluid flow from said bottom portion of said luer-lock-bearing member to said top portion of said luer-lock-bearing member.

According to still another aspect of the invention, there is provided a vial adapter for use in transferring fluid from a vial, the vial having a top end and a bottom end, the top end of the vial being sealed with a septum, said vial adapter comprising (a) a hollow piercing member adapted to puncture a septum of a vial; and (b) a generally tubular body, said generally tubular body having a top, an open bottom and a side, said side extending from said top to said open bottom, said generally tubular body defining an inner cavity down into which said hollow piercing member extends, said side being interiorly shaped to include at least one rib, said at least one rib being dimensioned to permit an uncapped vial having an exposed septum to be inserted sufficiently upwardly into said inner cavity from said open bottom to permit said exposed septum to be pierced by said hollow piercing member while preventing a capped vial having a covered septum from being inserted sufficiently upwardly into said inner cavity from said open bottom to permit said capped vial from contacting said hollow piercing member.

For purposes of the present specification and claims, various relational terms like “top,” “bottom,” “proximal,” “distal,” “upper,” “lower,” “front,” and “rear” are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 4(*d*) is a longitudinal section view of the needle-bearing member of FIG. 4(*c*) taken along line 1-1;

FIG. 4(*e*) is a longitudinal section view of the needle-bearing member of FIG. 4(*c*) taken along line 2-2;

FIG. 4(*f*) is an enlarged fragmentary section view of the needle-bearing member of FIG. 4(*c*) taken along line 2-2;

DETAILED DESCRIPTION OF PREFERRED EMBODIMENTS

Figure 1:
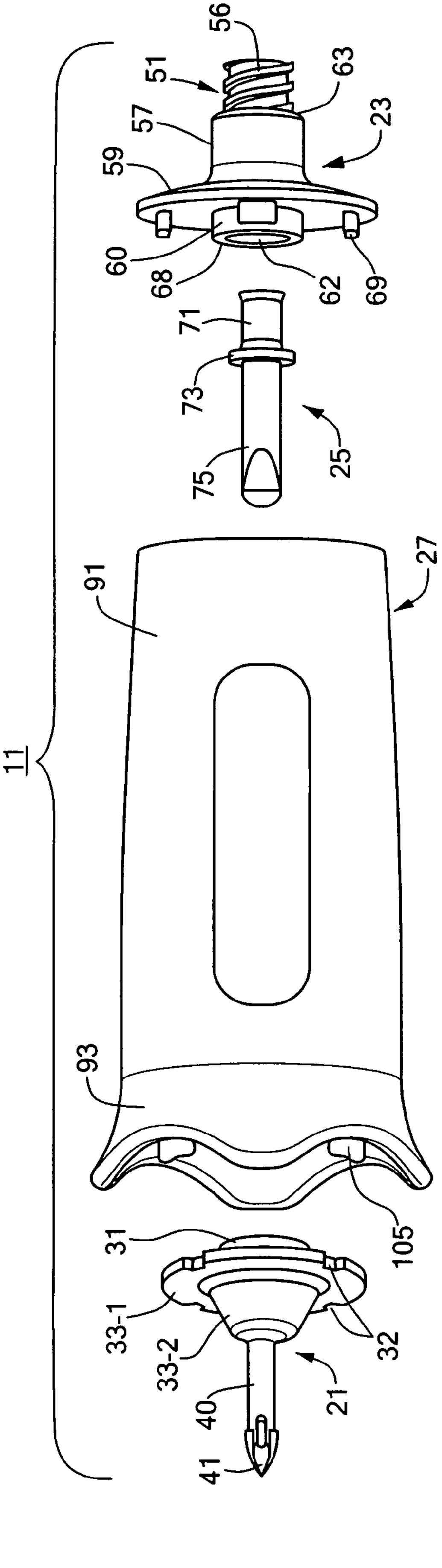
FIG. 1 is a partially exploded, perspective view of a first embodiment of a vial adapter constructed according to the teachings of the present invention.
Figure 2:
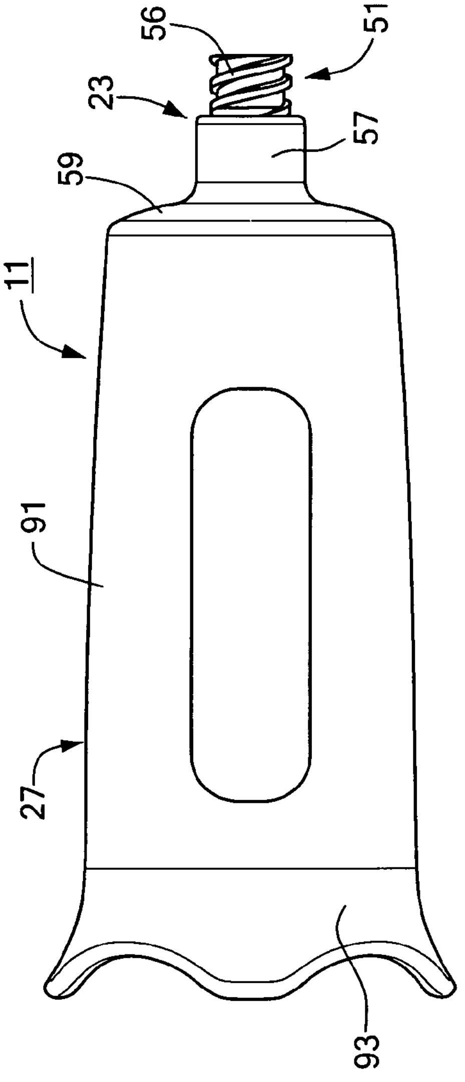
FIG. 2 is a side view of the vial adapter shown in FIG. 1.
Figure 3:
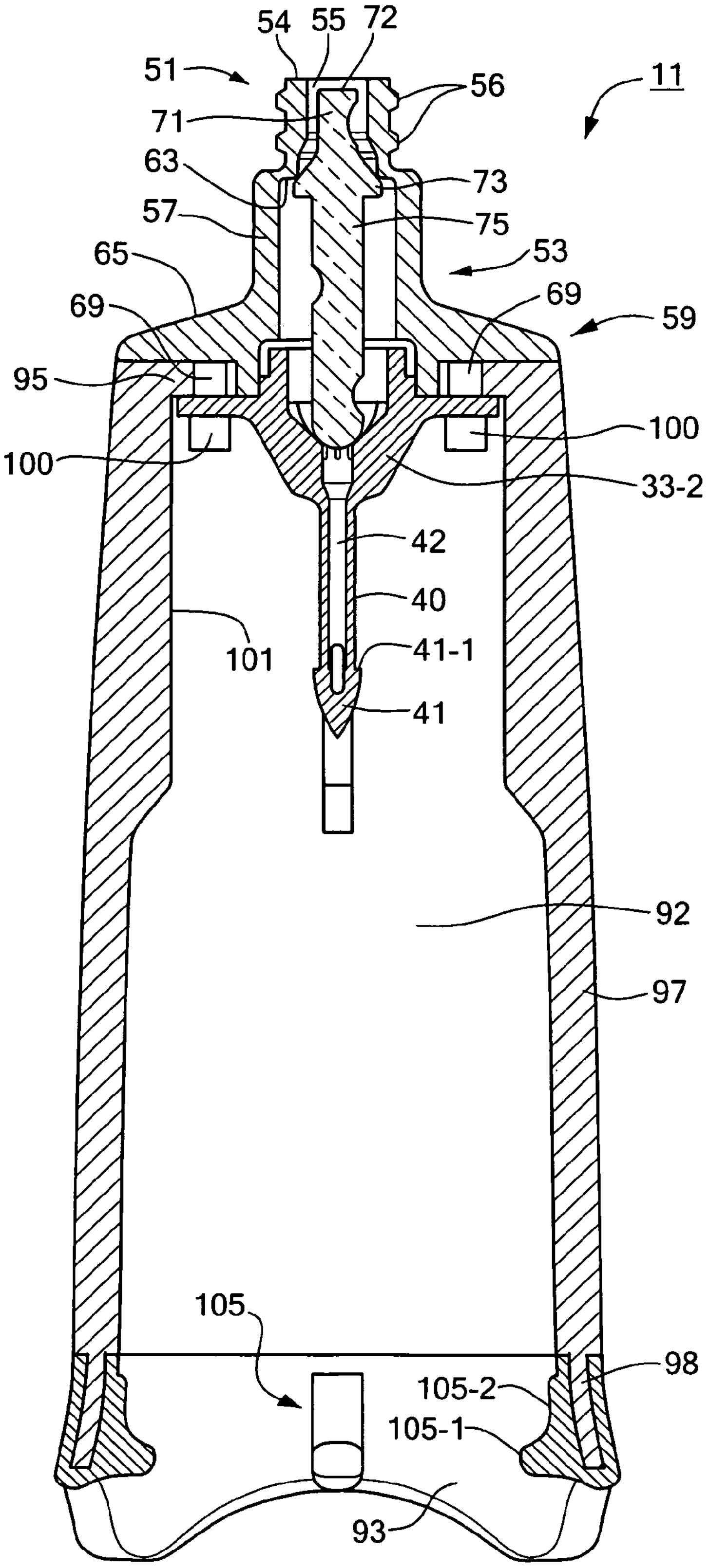
FIG. 3 is a longitudinal section view of the vial adapter shown in FIG. 1.
Figure 4A:
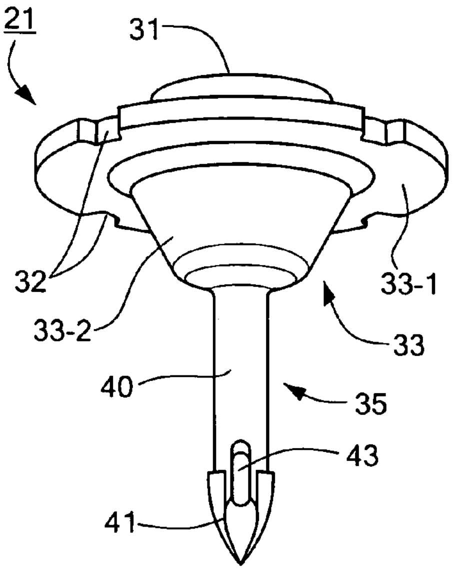
FIGS. 4(*a*) through 4(*c*) are bottom perspective, bottom and top views, respectively, of the needle-bearing member shown in FIG. 1.
Figure 4B:
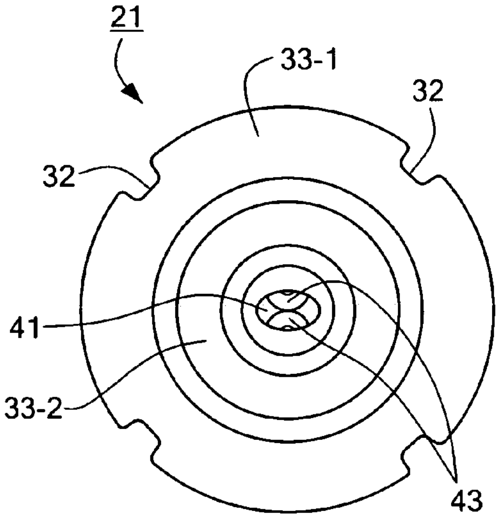
Figure 4C:
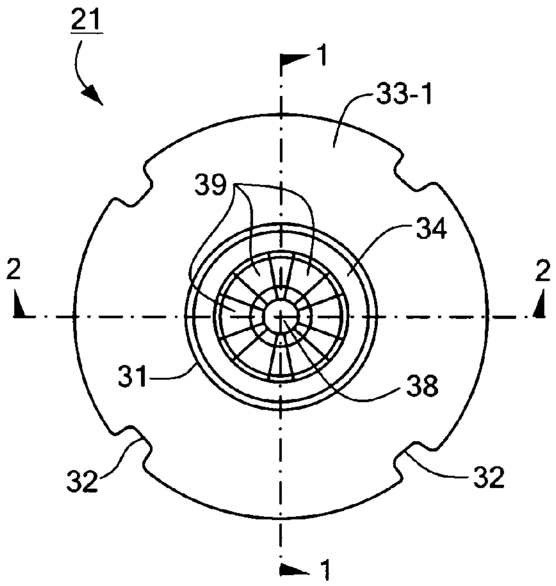
Figure 4D:
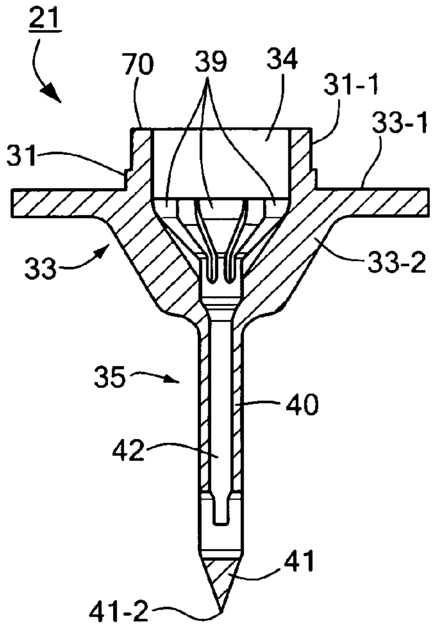
Figure 4F:
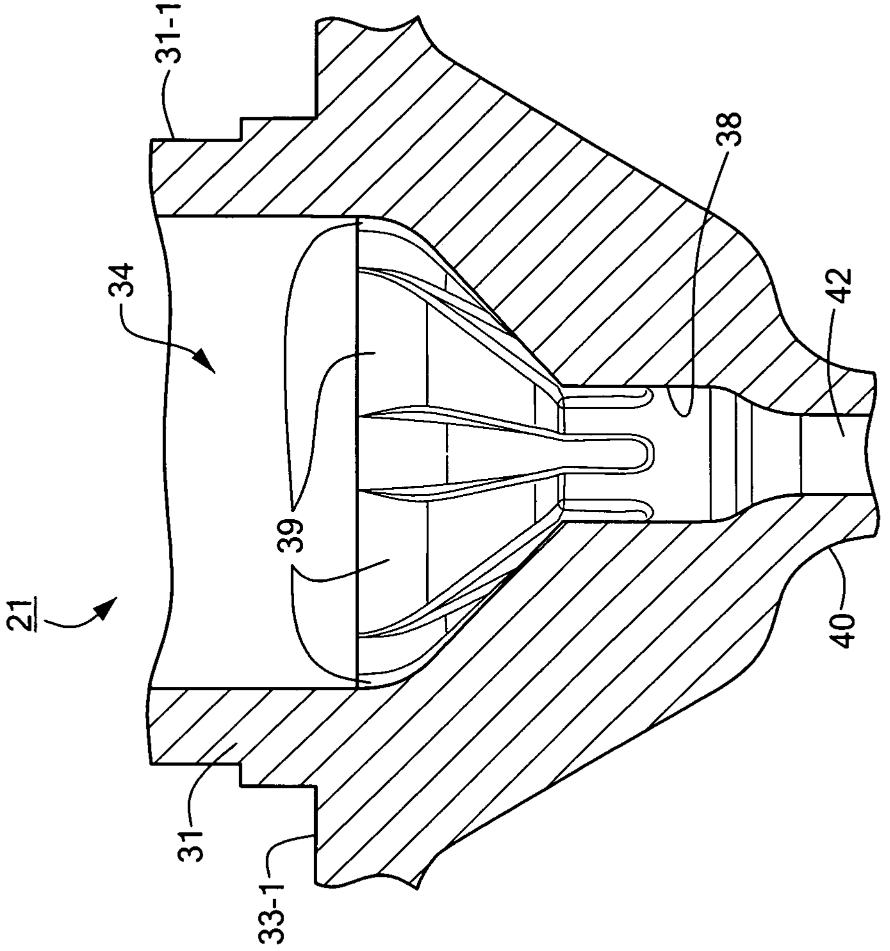
Figure 4E:
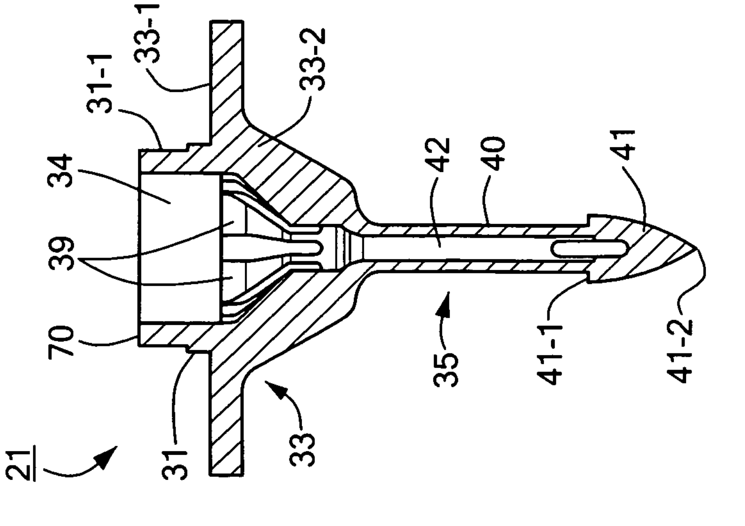
Figure 5A:
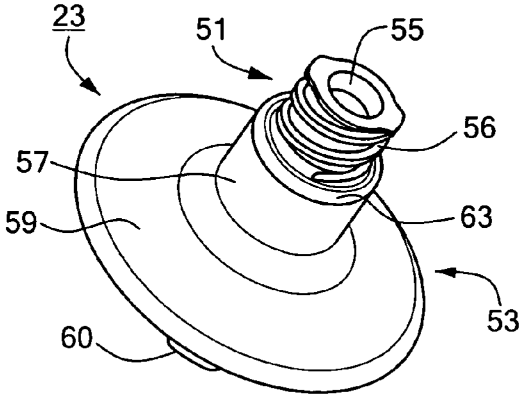
FIGS. 5(*a*) through 5(*d*) are top perspective, bottom perspective, longitudinal section and bottom views, respectively, of the luer-lock-bearing member shown in FIG. 1.
Figure 5B:
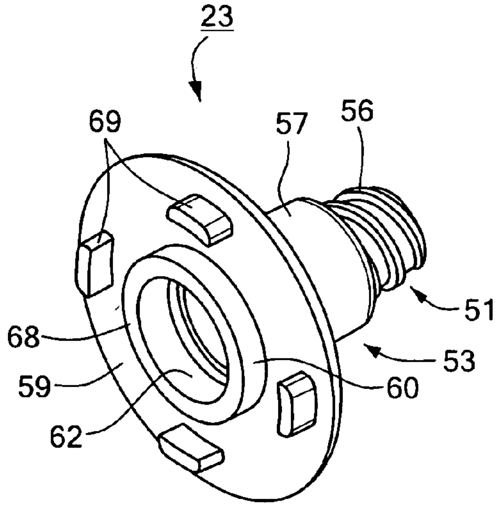
Figure 5C:
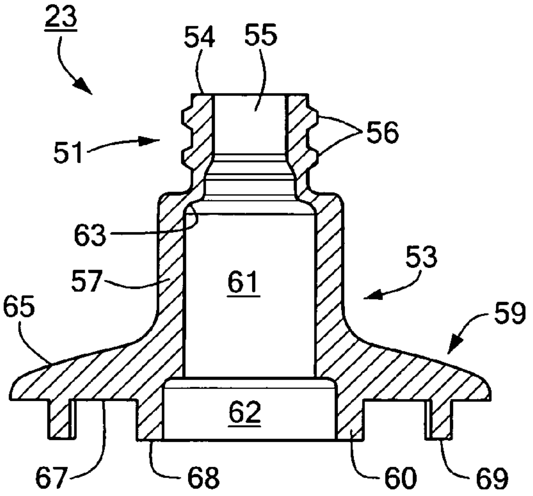
Figure 5D:
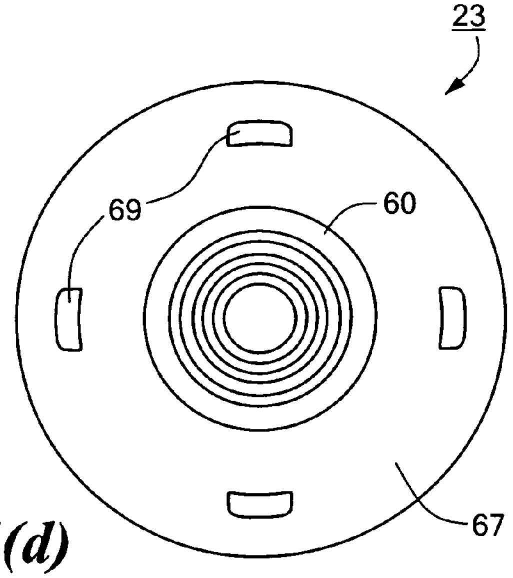
Figure 6D:
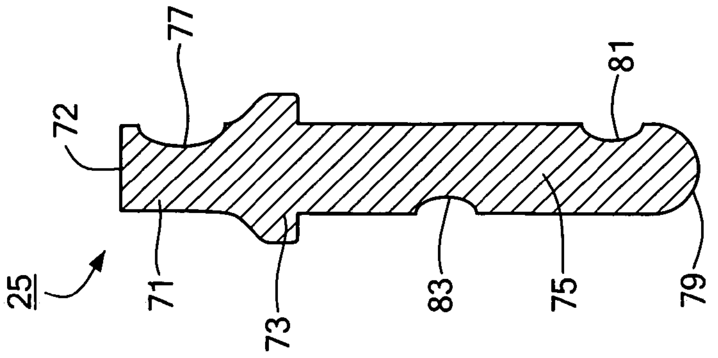
FIGS. 6(*a*) through 6(*d*) are front, rear, side and longitudinal section views, respectively, of the valve shown in FIG. 1.
Figure 6C:
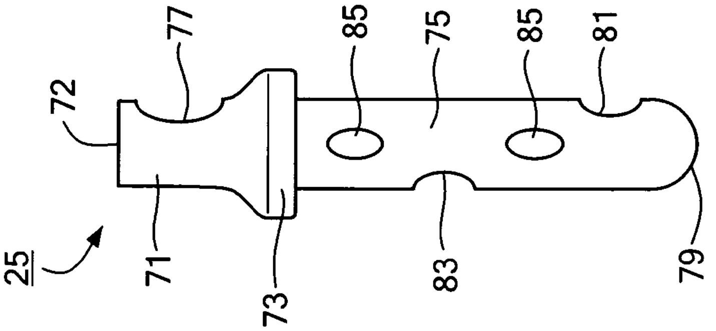
Figure 6B:
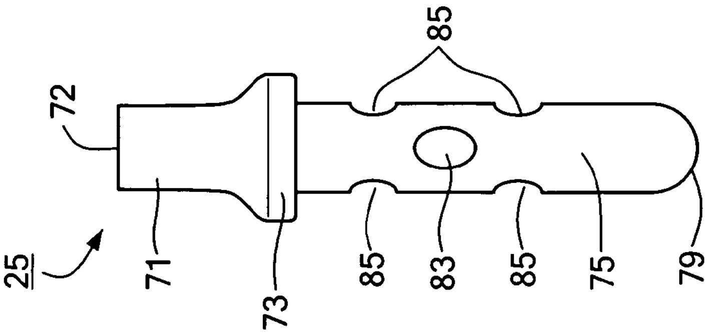
Figure 6A:
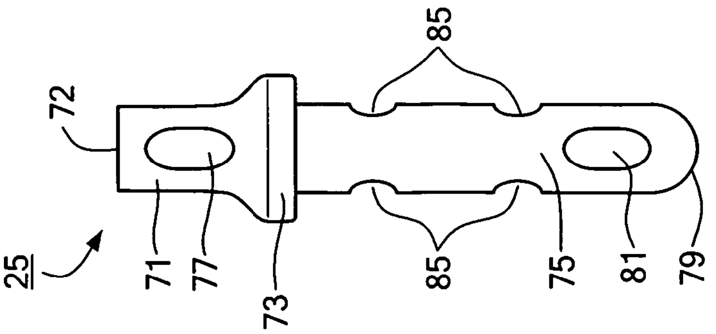
Figure 7C:
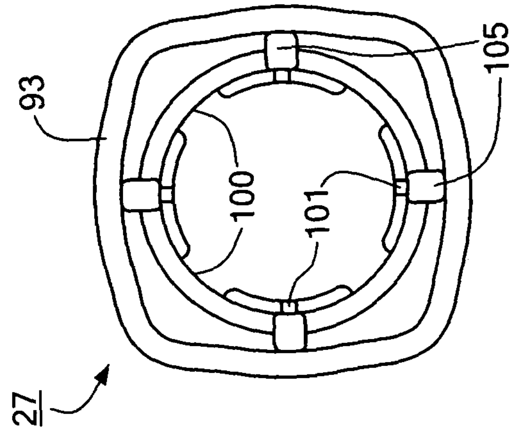
FIGS. 7(*a*) through 7(*d*) are top perspective, bottom perspective, bottom, enlarged longitudinal section, and enlarged fragmentary section views, respectively, of the body shown in FIG. 1.
Figure 7B:
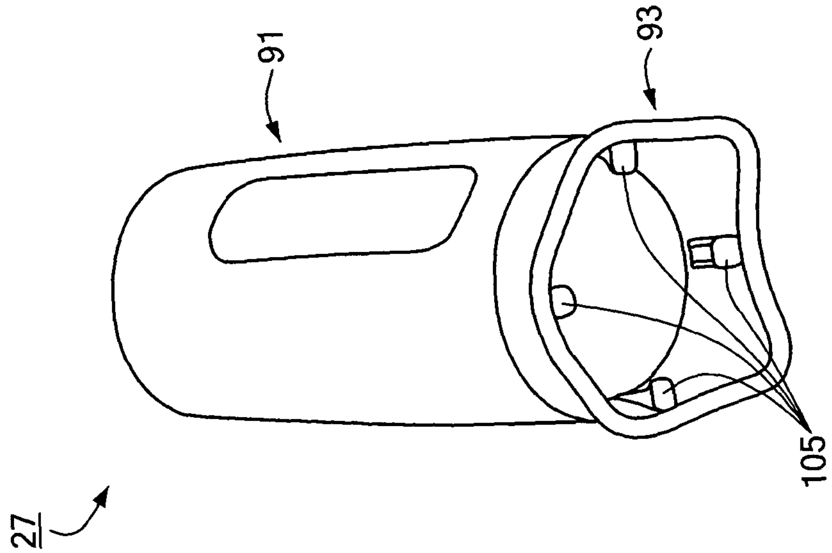
Figure 7A:
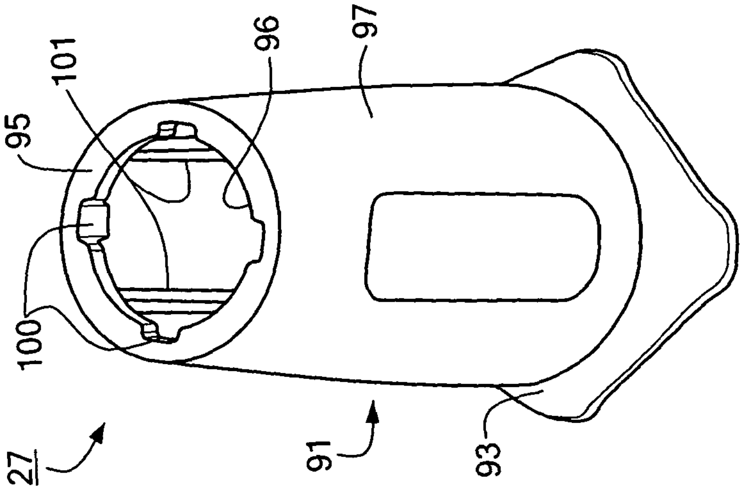
Figure 7E:
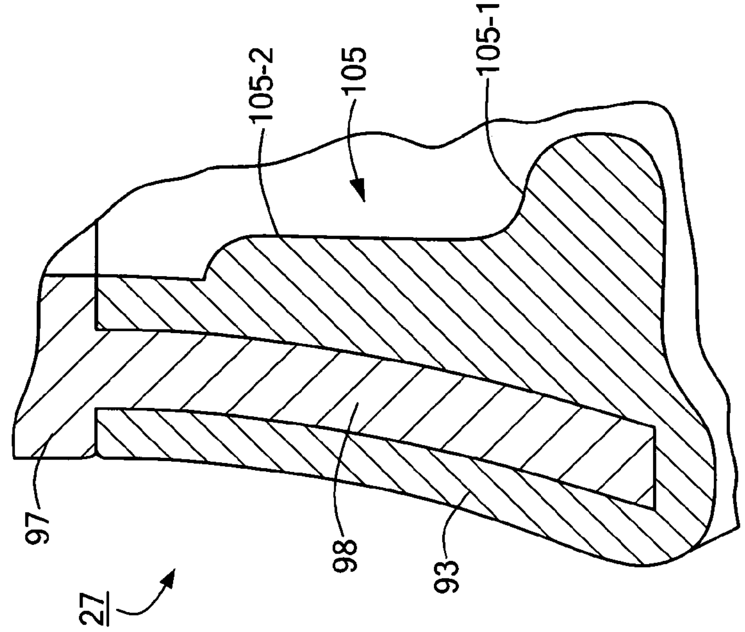
Figure 7D:
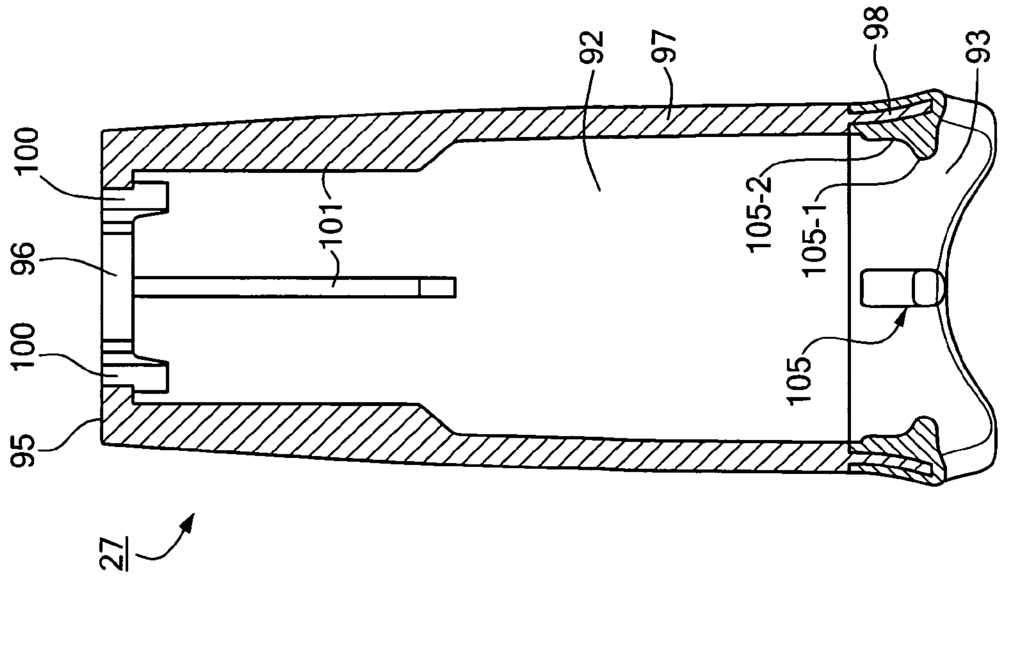
Figure 8A:
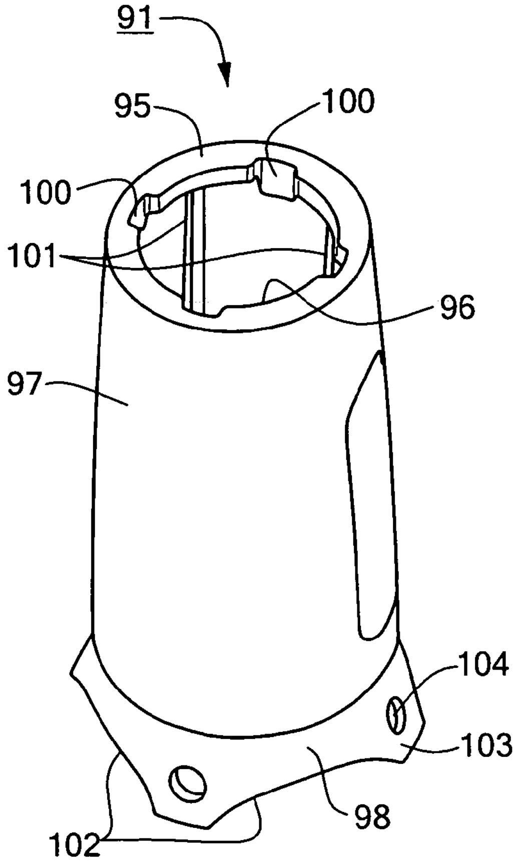
FIGS. 8(*a*) through 8(*e*) are top perspective, bottom perspective, top, side, and enlarged longitudinal section views, respectively, of the sleeve shown in FIG. 1.
Figure 8B:
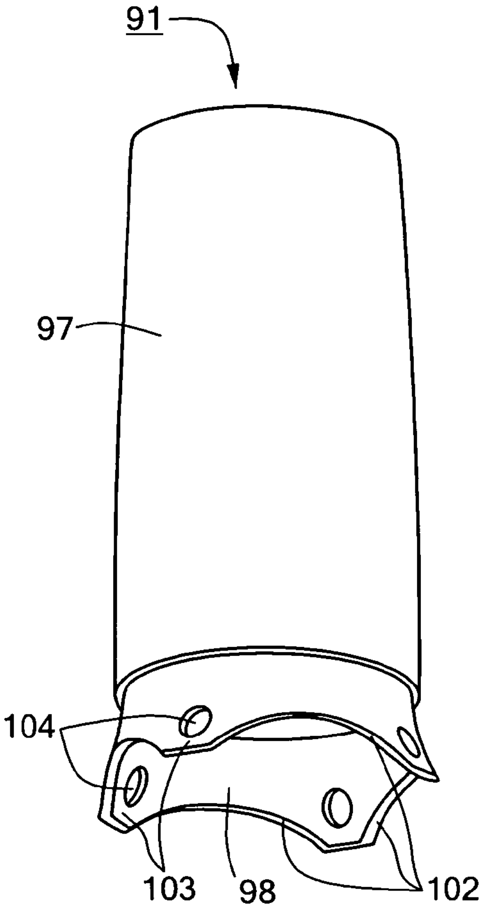
Figure 8C:
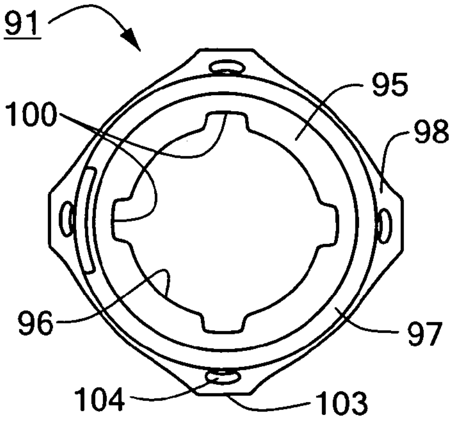
Figure 8D:
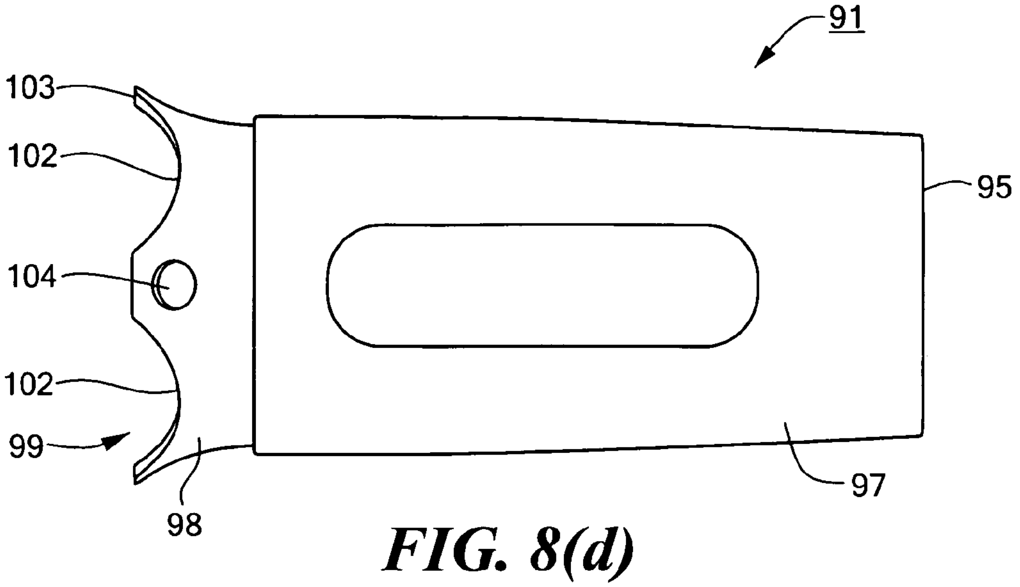
Figure 8E:
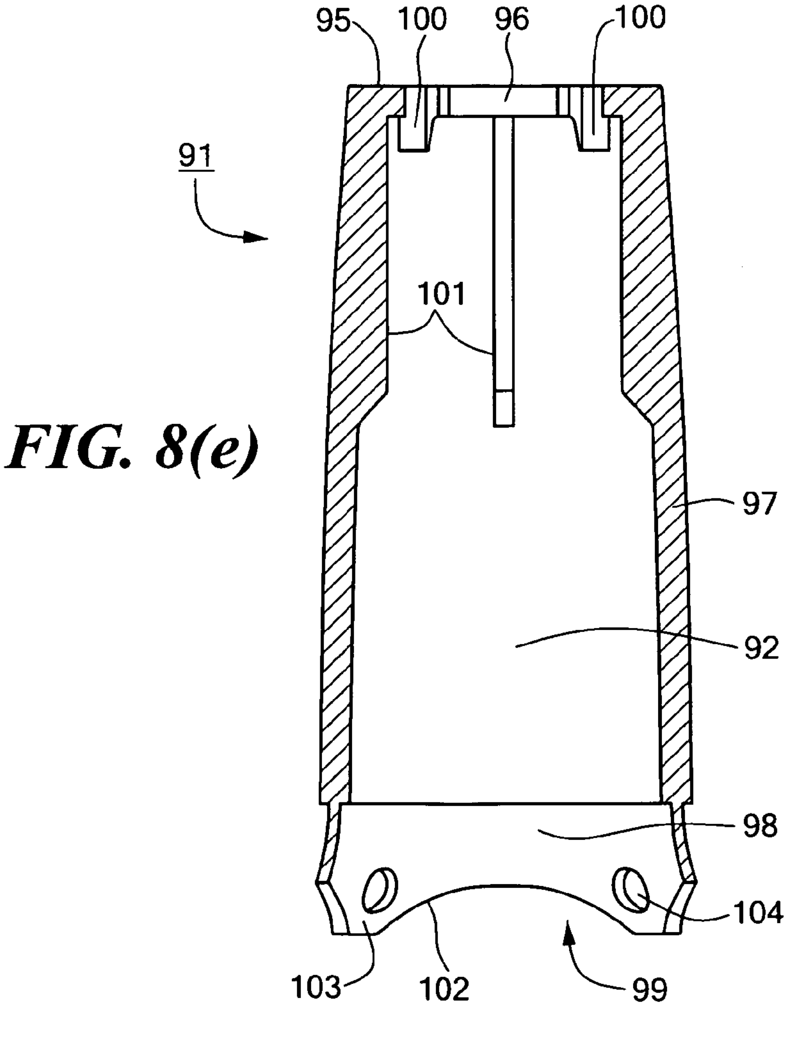

Referring now to FIGS. 1 through 3, there are shown partially exploded perspective, side and longitudinal section views, respectively, of a first embodiment of a vial adapter constructed according to the teachings of the present invention, said vial adapter being represented generally by reference numeral 11.

Adapter 11 comprises a needle-bearing member 21, a luer-lock-bearing member 23, a valve 25, and a body 27.

Needle-bearing member 21, which is also shown separately in FIGS. 4(*a*) through 4(*f*), is a unitary structure, preferably made of a rigid, amorphous, molded plastic. (Where adapter 11 is intended to be used with vials containing dimethylsulfoxide (DMSO), needle-bearing member 21 is preferably made of TOPAS polymer (Ticona, Summit, N.J.), a thermoplastic olefin of amorphous structure (also known as a cyclo-olefin copolymer or "COC"). Where adapter 11 is intended to be used with vials not containing DMSO, needle-bearing member 21 may be made of TOPAS polymer or another rigid amorphous material, such as a polycarbonate or an acrylic.) Member 21 is shaped to include a top portion 31, an intermediate portion 33 and a bottom portion 35. Top portion 31 and intermediate portion 33 are hollow and jointly define a cavity 34 having a cylindrical upper section and a generally conical lower section. Top portion 31 of member 21 is generally cylindrical in shape and includes an area of decreased wall thickness 31-1 to provide a space into which material may flow as a consequence of ultrasonically welding together needle-bearing member 21 and luer-lock-bearing member 23, as will be further described below.

Intermediate portion 33 of member 21 includes an annular top section 33-1 and a generally conical bottom section 33-2. Annular top section 33-1 is provided with a plurality of rectangular transverse notches 32 equally spaced about its periphery, the purpose of notches 32 to be described below. (Although four notches 32 are shown in the present embodiment, the present invention is not limited to an embodiment having exactly four notches 32; accordingly, annular top section 33-1 may include more than four notches 32 or fewer than four (including zero) notches 32.) Conical bottom section 33-2 of intermediate portion 33, which tapers downwardly, is interiorly shaped to define a central opening 38 peripherally surrounded by a plurality of spaced apart valve supports 39 extending upwardly and radially outwardly therefrom. (Although six valve supports 39 are shown in the present embodiment, the present invention is not limited to an embodiment having exactly six valve supports 39; accordingly, bottom section 33-2 may include more than six supports 39 or fewer than six (including zero) supports 39. Moreover, the present invention is not limited to valve supports 39 having the specific shape shown.)

Lower portion 35, which functions as a hollow needle for conducting fluid from a vial, is shaped to include a shaft 40 and a head 41, shaft 40 and head 41 being considerably more narrow in outer diameter than intermediate portion 33. Shaft 40, which is joined at its upper end to intermediate portion 33 and extends downwardly perpendicularly thereto, is an elongated structure sized to traverse the thickness of a vial septum. Shaft 40 is shaped to include a longitudinal bore 42, bore 42 being aligned with opening 38. Head 41, which is disposed at the bottom end of shaft 40, has a substantially flat top end 41-1 that is enlarged relative to shaft 40 and a bottom end 41-2 that is in the form of a sharp tip adapted to pierce a vial septum. As can readily be appreciated, the size and shape of top end 41-1 of head 41 prevent the withdrawal of head 41 from a vial after head 41 has been inserted through a vial septum. A pair of side openings 43 are provided in lower portion 35 at the juncture of shaft 40 and head 41 to provide fluid access to bore 42.

It should be noted that, although head 41 is a substantially two-sided head in the present embodiment, the present invention is not limited to a two-sided head and may include heads having fewer than two sides or more than two sides.

Luer-lock-bearing member 23, which is also shown separately in FIGS. 5(*a*) through 5(*d*), is a unitary structure, preferably made of a rigid, amorphous, molded plastic. (Where adapter 11 is intended to be used with vials containing dimethylsulfoxide (DMSO), luer-lock-bearing member 23 is preferably made of TOPAS polymer. Where adapter 11 is intended to be used with vials not containing DMSO, luer-lock-bearing member 23 may be made of TOPAS polymer or another rigid amorphous material, such as a polycarbonate or an acrylic.) Member 23 is shaped to include an upper portion 51 and a lower portion 53. Upper portion 51, which is in the form of a female luer-lock adapted for locking engagement to a needle-less syringe, is a tubular structure having a bore 55 adapted to receive a medical luer and an external thread 56 adapted to engage a mating thread on a syringe for lockably engaging the medical luer.

Lower portion 53 is a generally tubular structure shaped to include a generally cylindrical upper section 57, a radially expanded, annular intermediate section 59 and a generally cylindrical lower section 60. Upper section 57 and intermediate section 59 jointly define a cylindrical bore 61, and intermediate section 59 and lower section 60 jointly define a cylindrical bore 62, bores 61 and 62 being aligned with bore 55 for fluid communication therewith. Because upper section 57 and bore 61 are greater in diameter than upper portion 51 and bore 55, respectively, a radial wall 63 interconnects the top end of upper section 57 and the bottom end of upper portion 51.

Intermediate section 59 is shaped to include a top surface 65 and a bottom surface 67, top surface 65 sloping downwardly as it expands radially outwardly, bottom surface 67 being substantially flat. A plurality of projections 69, the purpose of which will be described below, extend downwardly from bottom surface 67. (Although four projections 69 are shown in the present embodiment, the present invention is not limited to an embodiment having exactly four projections 69; accordingly, annular section 59 may include more than four projections 69 or fewer than four (including zero) projections 69. Moreover, although projections 69 are shaped in the present embodiment as slightly-curved rectangular blocks, projections 69 need not take such a shape.)

Lower section 60 of luer-lock-bearing member 23 has an open bottom end 68. Top portion 31 of needle-bearing member 21 has an open top end 70, top portion 31 being inserted through bottom end 68 and into bore 62 and ultrasonically welded to luer-lock-bearing member 23.

Valve 25, which is also shown separately in FIGS. 6(*a*) through 6(*d*), is a solid, unitary structure preferably made of a resiliently flexible silicone or similar material. Valve 25, which is commercially available from Medegen Holdings, LLC (Scottsdale, Ariz.) and which may be identical to valve element 90*b* of U.S. Pat. No. 5,782,816 (the disclosure of which is incorporated herein by reference), is shaped to include an upper portion 71, an intermediate portion 73 and a lower portion 75. Upper portion 71 is a generally cylindrical structure. As can be seen in FIG. 3, when vial adapter 11 is not connected to a syringe, upper portion 71 is snugly received within bore 55 of luer-lock-bearing member 23, with the top surface 72 of upper portion 71 being recessed or spaced downwardly from a top surface 54 of upper portion 51. (In an alternative embodiment (not shown), the top surface 72 of upper portion 71 lies flush with top surface 54 of upper portion 51.) A notch 77, preferably in the shape of a scalloped area, is provided along a side wall of upper portion 71, notch 77 facilitating the folding or deflection of valve 25 when adapter 11 is coupled to a syringe, as will be further discussed below. Intermediate portion 73 of valve 25 is a generally cylindrical element of increased diameter as compared to upper portion 71 and lower portion 75. As seen in FIG. 3, when valve 25 is not connected to a syringe, the top surface of intermediate portion 73 is pressed against annular wall 63 of luer-lock-bearing member 23 in such a manner as to prevent fluid communication between bore 61 and bore 55. Lower portion 75 of valve 25 is an elongated structure having a bottom end 79 seated on supports 39 of needle-bearing member 21. A front notch 81, a rear notch 83 and a plurality of side notches 85 are provided on lower portion 75, all of notches 81, 83 and 85 preferably having a scalloped shape. As will become apparent from the discussion below, notches 81, 83 and 85 also facilitate the folding or deflection of valve 25 when adapter 11 is coupled to a syringe.

Body 27, which is also shown separately in FIGS. 7(*a*) through 7(*d*), includes a sleeve 91 and a jacket 93, jacket 93 being insert-molded over a lower portion of sleeve 91. Sleeve 91 (also shown separately in FIGS. 8(*a*) through 8(*e*)) is a unitary structure, preferably made of a rigid, amorphous, molded plastic. (Where adapter 11 is intended to be used with vials containing dimethylsulfoxide (DMSO), sleeve 91 is preferably made of TOPAS polymer. Where adapter 11 is intended to be used with vials not containing DMSO, sleeve 91 may be made of TOPAS polymer or another rigid amorphous material, such as a polycarbonate or an acrylic.) Sleeve 91 is shaped to include an annular top wall 95, an upper side wall 97, a lower side wall or skirt 98, and an open bottom 99. Top wall 95, side wall 97 and skirt 98 jointly define a cavity 92.

Annular top wall 95 is shaped to define a central opening 96 and a plurality of transverse slots 100 spaced around its inner periphery and facing opening 96. Bottom surface 67 of luer-lock-bearing member 23 is seated directly on top of annular top wall 95 of sleeve 91, with blocks 69 of annular section 59 mating with slots 100 and with the bottom portion of tubular section 57 extending downwardly through opening 96. The mating together of blocks 69 and slots 100 serves to keep luer-lock-bearing member 23 from rotating relative to sleeve 91, a feature that is particularly important in view of the fact that a rotational force is applied to luer-lock-bearing member 23 when a syringe is screwed onto or unscrewed from adapter 11.

Upper side wall 97 of sleeve 91 is generally cylindrical in shape but expands slightly in diameter from top to bottom. Needle-bearing member 21 is disposed within upper side wall 97, with top wall 95 seated directly on top of top portion 31 of needle-bearing member 21. The inside surface of upper side wall 97 is shaped to include a plurality of ribs 101 extending downwardly approximately one-third the distance from top wall 95 to open bottom 99. Ribs 101 are appropriately dimensioned to limit the upward insertion into sleeve 91 of a vial whose protective cover has not yet been removed and, therefore, whose septum has not yet been exposed for puncturing. In this manner, ribs 101 protect head 41 of needle-bearing member 21 against possible damage that may result from an accidental attempt to puncture a covered or unexposed septum. In addition, ribs 101 also serve to center within wall 97 a vial whose cover has been removed so that head 41 of needle-bearing member 21 may be properly aligned with the exposed septum of said vial. Ribs 101 also mate with notches 32 of needle-bearing member 21, thereby preventing rotational movement of needle-bearing member 21 relative to sleeve 91, particularly when a syringe is screwed onto or unscrewed from adapter 11.

Skirt 98 is a generally square or four-sided structure that flares outwardly in diameter from side wall 97 to open bottom 99. A concave recess 102, which is dimensioned to receive a user's thumb when a vial is inserted up into sleeve 91, is formed along the bottom edge of each of the four sides of skirt 98, each pair of adjacent recesses 102 defining therebetween a tab 103 having a transverse opening 104 (the purpose of which will be described below).

It is believed that the above-described shape of skirt 98 is desirable in that it fits ergonomically in the hand(s) of a user, not only when loading a vial into sleeve 91 but also when attaching a syringe to adapter 11 or when drawing fluid from a vial through adapter 11 into a syringe. In addition, the non-cylindrical shape of skirt 98 prevents adapter 11 from rolling when adapter 11 is laid on its side on a table top or like surface. Notwithstanding the above, the present invention is not limited to a square or four-sided skirt 98, and skirt 98 may include more than four sides or fewer than four (including zero) sides.

Sleeve 91 is preferably optically clear so that the contents of a vial may be observed through sleeve 91. In addition, although not shown in the present embodiment, sleeve 91 may include markings along side wall 97 to indicate the volume of fluid present within a vial disposed within sleeve 91.

Jacket 93 is overmolded onto skirt 98 of sleeve 91 and is anchored to sleeve 91 through openings 104 in skirt 98. Jacket 93, which is preferably made of a resilient, easily gripped material, such as a rubber or SANTOPRENE® thermoplastic elastomer (Advanced Elastomer Systems, LP, Akron, Ohio), is shaped to include a plurality of inwardly-facing L-shaped latches 105. (Although four latches 105 are shown in the present embodiment, the present invention is not limited to an embodiment having exactly four latches 105; accordingly, jacket 93 may include more than four latches 105 or fewer than four latches 105.) Latches 105, each of which includes a radially extending arm 105-1 and a longitudinally-extending arm 105-2, are adapted to flex radially outwardly a small distance as a vial is inserted upwardly past arm 105-1. However, once a vial has been inserted past arm 105-1, latch 105 returns to its original position, and the top surface of arm 105-1 slides in underneath the bottom surface of the inserted vial, causing the vial to be securely retained within body 27.

It should be understood that, although latches 105 are positioned to engage the bottom surface of an inserted vial, latches 105 could be positioned to engage other portions of an inserted vial.

Figure 9:
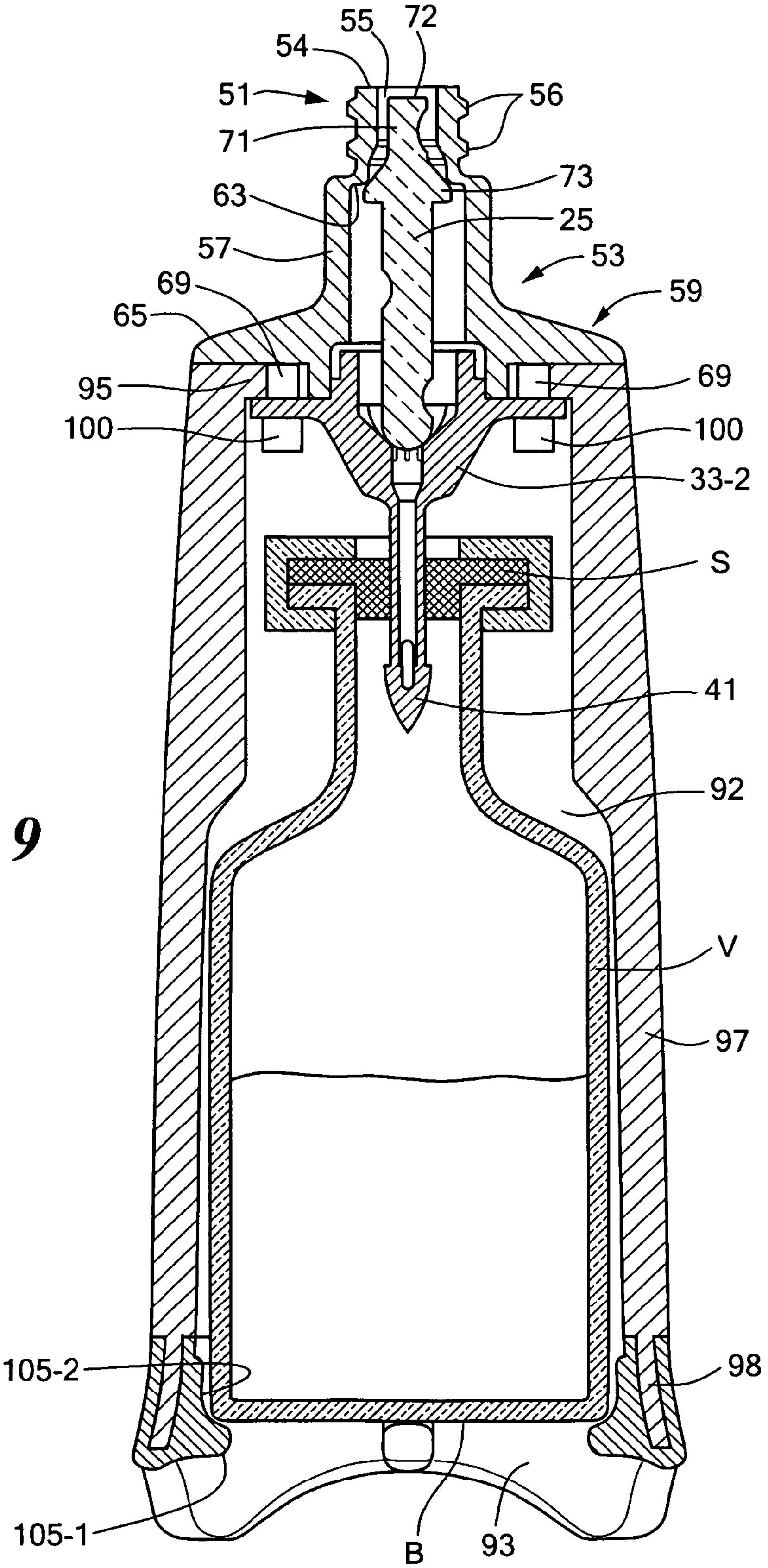
FIG. 9 is a longitudinal section view of the vial adapter of FIG. 1, with a medicine vial shown mounted therein.

To transfer the fluid contents of a medicine vial to a needle-less syringe using adapter 11, one preferably first secures the vial to adapter 11. (One could connect adapter 11 to syringe 111 prior to connecting adapter 11 to a vial, but this would involve attaching adapter 11 to the vial while valve 25 of adapter 11 is in an open state.) To connect a vial to adapter 11, one removes the protective cap of the vial (if such a cap is present) and inserts the vial V upwardly through the open bottom end of body 27 until head 41 of needle-bearing member 21 is inserted completely through the septum S of the vial V, and the bottom surface B of the vial V is inserted past the radially-extending arms 105-1 of latches 105 (see FIG. 9). With the medicine vial thus secured to adapter 11, it cannot be removed from adapter 11 without great effort and/or damage to adapter 11 or the vial. Consequently, it can be seen that adapter 11 greatly deters the above-described practice of combining the remnant quantities of a plurality of vials and, instead, promotes the use of one vial for one patient. Moreover, prior to attachment of a syringe to adapter 11, it can be seen that valve 25 prevents fluid from escaping from adapter 11 by sealing off bore 55 from bore 61. Accordingly, if the vial contains a fluid that should be shaken prior to administration to a patient, the vial and adapter 11 may be shaken together as valve 25 will prevent any leakage of the fluid into bore 55.

Figure 10:
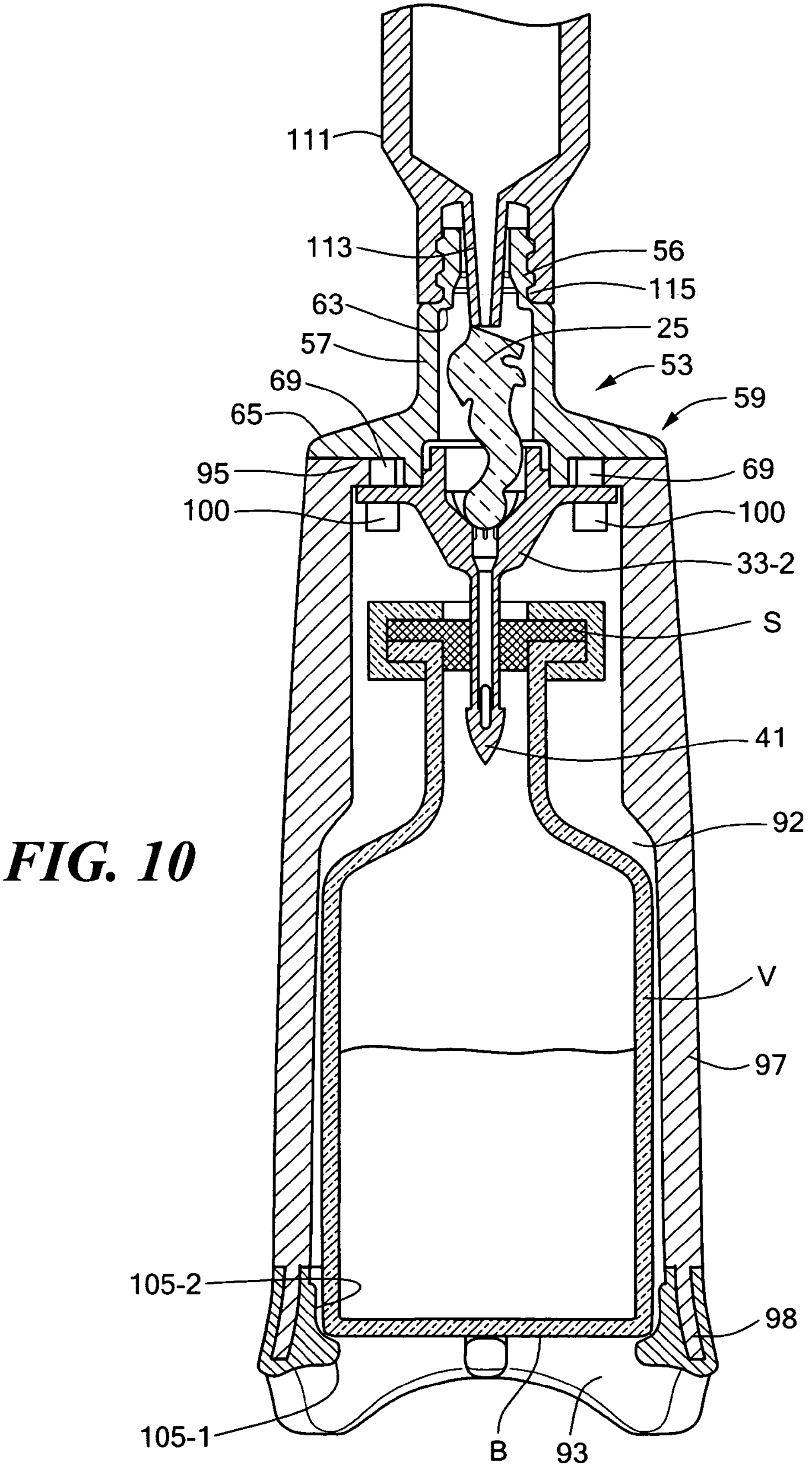
FIG. 10 is a fragmentary longitudinal section view of the vial adapter of FIG. 1, with a medicine vial shown mounted therein and a needleless syringe connected thereto.

Referring now to FIG. 10, when adapter 11 is connected to a needle-less syringe 111, i.e., by inserting the luer tip 113 of the syringe 111 into upper portion 51 and matingly engaging the thread 115 on the syringe 111 with thread 56 on upper portion 51, luer tip 113 of syringe 111 causes valve 25 to be folded and/or deflected in such a way as to permit fluid to flow from the vial V through bore 61 and into syringe 111. After a desired amount of fluid has been transferred from vial V to syringe 111, syringe 111 may be disconnected from adapter 11, thereby causing valve 25 to return to its original closed position (see FIG. 9).

It should be understood that one could modify adapter 11, for example, by removing valve 25 from the chamber jointly defined by needle-bearing member 21 and luer-lock-bearing member 23 and, instead, mounting valve 25 in a connector having a male luer end removably mountable on tubular member 51 of luer-lock-bearing member 23 and a female luer end removably mountable on a needleless syringe.

Figure 11A:
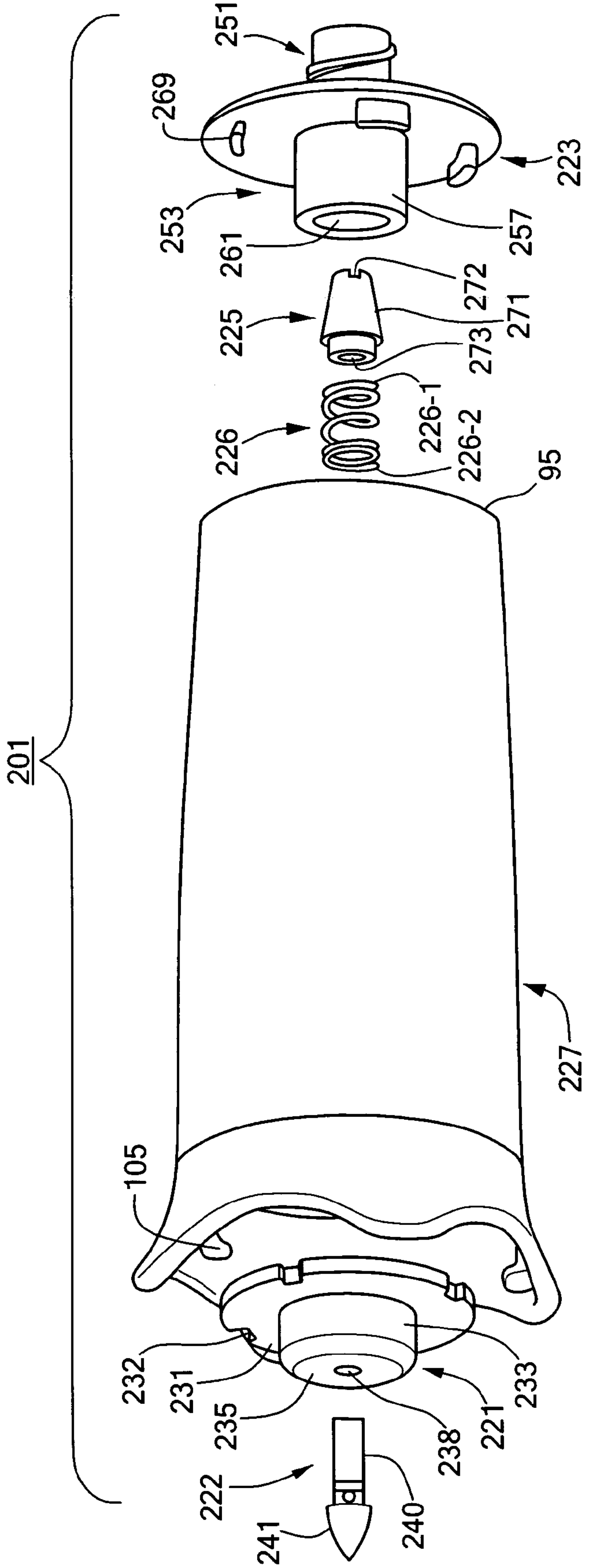
FIGS. 11(*a*) and 11(*b*) are partially exploded perspective and perspective, partly in section, views, respectively, of a second embodiment of a vial adapter constructed according to the teachings of the present invention.
Figure 11B:
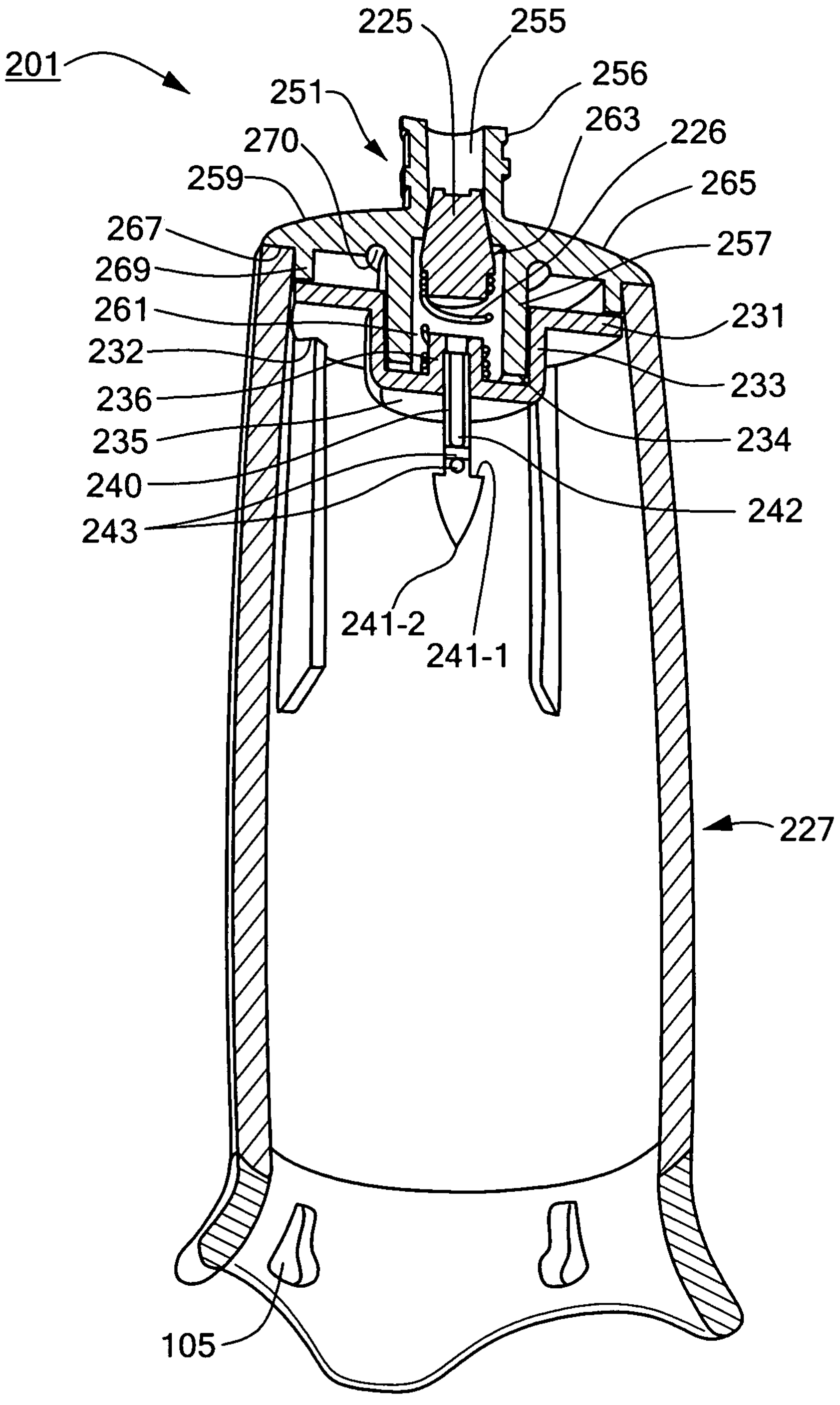

Referring now to FIGS. 11(*a*) and 11(*b*), there are shown partially exploded perspective and perspective, partly in section, views, respectively, of a second embodiment of a vial adapter constructed according to the teachings of the present invention, said vial adapter being represented generally by reference numeral 201.

Vial adapter 201 comprises a needle-holding member 221, a needle 222, a luer-lock-bearing member 223, a valve 225, a spring 226, and a body 227.

Needle-holding member 221 is a unitary member, preferably made of a rigid, amorphous, molded plastic. (Where adapter 201 is intended to be used with vials containing dimethylsulfoxide (DMSO), needle-holding member 221 is preferably made of TOPAS polymer. Where adapter 201 is intended to be used with vials not containing DMSO, needle-holding member 221 may be made of TOPAS polymer or another rigid amorphous material, such as a polycarbonate or an acrylic.) Member 221 is shaped to include a top wall 231, a side wall 233 and a bottom wall 235, all of which together define a generally cylindrical cavity 234. Top wall 231 is generally annular in shape and is provided with a plurality of rectangular transverse notches 232 equally spaced about its periphery, notches 232 having a similar purpose to notches 32 of adapter 11. (Although four notches 232 are shown in the present embodiment, the present invention is not limited to an embodiment having exactly four notches 232; accordingly, top wall 231 may include more than four notches 232 or fewer than four (including zero) notches 232.)

Side wall 233, which is generally circular in shape, has a smaller outer diameter than does top wall 231. Bottom wall 233 is also generally circular in shape and includes a centrally disposed sleeve 236 extending upwardly a short distance. A small transverse opening 238 is centrally located in bottom wall 233 in alignment with sleeve 236.

Needle 222 is a unitary member, preferably made of a rigid, amorphous, molded plastic, stainless steel or the like. (Where adapter 201 is intended to be used with vials containing dimethylsulfoxide (DMSO), needle 222 is preferably made of TOPAS polymer. Where adapter 201 is intended to be used with vials not containing DMSO, needle 222 may be made of TOPAS polymer or another rigid amorphous material, such as a polycarbonate or an acrylic.) Needle 222 is shaped to include a shaft 240 and a head 241. Shaft 240, which is fixedly mounted at its upper end within sleeve 236 and extends downwardly through opening 238, is an elongated structure sized to traverse the thickness of a vial septum. Shaft 240 is shaped to include a longitudinally-extending bore 242 and a pair of transverse openings 243 that permit fluid access to bore 242. Head 241, which is disposed at the bottom end of shaft 240, has a substantially flat top end 241-1 that is enlarged relative to shaft 240 and a bottom end 241-2 that is in the form of a sharp tip adapted to pierce a vial septum. As can readily be appreciated, the size and shape of top end 241-1 of head 241 prevent the withdrawal of head 241 from a vial after head 241 has been inserted through a vial septum.

Luer-lock-bearing member 223 is a unitary member, preferably made of a rigid, amorphous, molded plastic. (Where adapter 201 is intended to be used with vials containing dimethylsulfoxide (DMSO), luer-lock-bearing member 223 is preferably made of TOPAS polymer. Where adapter 201 is intended to be used with vials not containing DMSO, luer-lock-bearing member 223 may be made of TOPAS polymer or another rigid amorphous material, such as a polycarbonate or an acrylic.) Member 223 is shaped to include an upper portion 251 and a lower portion 253. Upper portion 251, which is in the form of a luer-lock adapted for attachment to a needle-less syringe, is a tubular structure having a bore 255 adapted to receive a medical luer and an external thread 256 adapted to engage a mating thread on a syringe for lockably engaging the medical luer. Lower portion 253 is shaped to include a tubular section 257 of generally cylindrical shape and an annular section 259, annular section 259 radially surrounding tubular section 257 at an intermediate location. Tubular section 257, the bottom end of which is snugly received in and ultrasonically welded to side wall 233 of needle-holding member 221, includes a longitudinal bore 261, bore 261 being aligned with bore 255 for fluid communication therewith. Because tubular section 257 has a greater diameter than does upper portion 251, a radial wall 263 interconnects the top end of tubular section 257 and the bottom end of upper portion 251.

Annular section 259 of lower portion 253 has an arcuate top surface 265 and a substantially flat bottom surface 267. A plurality of projections 269, which serve a similar purpose to projections 69 of adapter 11, extend downwardly from bottom surface 267. (Although four projections 269 are shown in the present embodiment, the present invention is not limited to an embodiment having exactly four projections 269; accordingly, annular section 259 may include more than four projections 269 or fewer than four (including zero) projections 269. Moreover, although projections 269 are shaped in the present embodiment as slightly-curved rectangular blocks, projections 269 need not take such a shape.) An annular groove 270 is provided in bottom surface 267 proximate to tubular section 257, groove 270 providing a space into which material may flow as a consequence of the ultrasonically welding together of tubular section 257 and intermediate portion 233.

Valve 225 is a solid, unitary member, which may be made of silicone or the like. Valve 225 is shaped to include an upper head portion 271 and a lower stem portion 273. Head portion 271, which is generally frustoconical in shape, is appropriately dimensioned to fit into bore 255 in such a way as to seal off bore 255 from bore 261. A recessed area 272 is provided on the top surface of head portion 271. Lower stem portion 273 is a generally cylindrical structure. Valve 225 is biased upwardly into bore 255 by spring 226, which has a first end 226-1 secured around lower stem portion 273 and a second end 226-2 secured around sleeve 236 of needle-holding member 221.

Body 227 is identical to body 27 of adapter 11, with annular top wall 95 of body 227 being sandwiched directly between bottom surface 267 of luer-lock-bearing member 223 and top wall 231 of needle-holding member 221.

Figure 12:
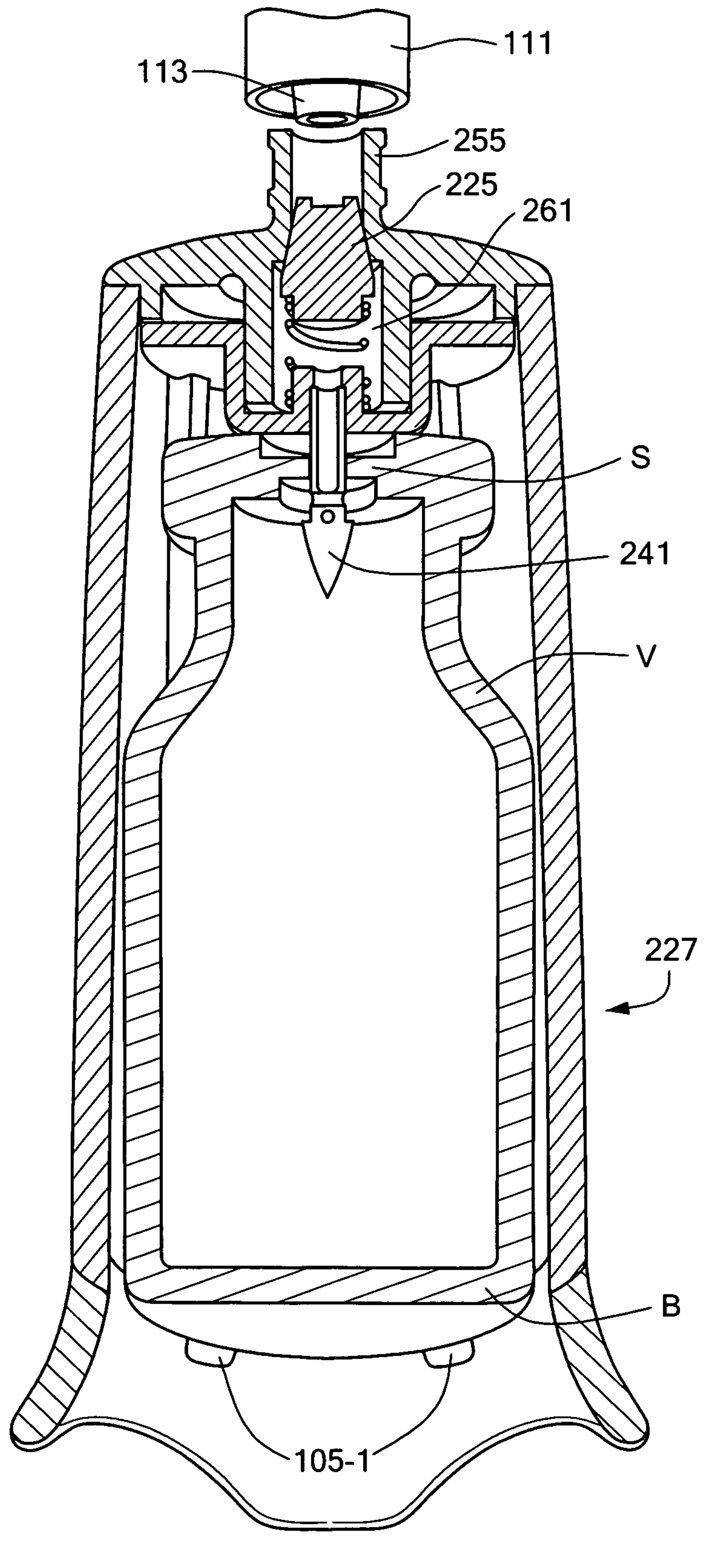
FIG. 12 is a perspective view, partly in section, of the vial adapter of FIGS. 11(*a*) and 11(*b*), the vial adapter being shown with a medicine vial mounted therein and a needleless syringe adapted for connection thereto.

Referring now to FIG. 12, the manner in which adapter 201 may be used to fluidly interconnect a medicine vial V to a needleless syringe 111 is illustrated. As can be seen, adapter 201 is preferably first connected to a medicine vial V by inserting the vial V upwardly through the open bottom end of body 227 until head 241 of needle 222 is inserted completely through the septum S of the vial V, and the bottom surface B of the vial V is inserted past the radially-extending arms 105-1 of latches 105. With the vial V thus secured to adapter 201, it cannot be removed from adapter 201 without great effort and/or damage to adapter 201 or vial V. Moreover, although fluid is permitted to flow from vial V to bore 261, valve 225 prevents fluid from flowing from bore 261 to bore 255. However, as can readily be appreciated, when a needleless syringe 111 is attached to adapter 201, the luer tip 113 of syringe 111 forces valve 225 downwardly to a point where fluid is permitted to flow from bore 261 to bore 255 (and into the syringe 111).

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A vial adapter for use in transferring fluid from a vial, the vial having a top end and a bottom end, the top end of the vial being sealed with a septum, said vial adapter comprising:

(a) a body, said body having a top end, a bottom end and an inner cavity, said inner cavity being dimensioned to receive the vial, with the bottom end of said body extending below the bottom end of the vial, wherein said bottom end is generally polygonal and wherein each of the sides of said bottom end of said body has a concave surface; and (b) a hollow piercing member extending downwardly into said inner cavity of said body for puncturing the septum of a vial disposed in said inner cavity.

2. The vial adapter as claimed in claim 1 wherein said body further includes at least one latch adapted to engage a vial disposed within said inner cavity for retaining the vial within said inner cavity.

3. The vial adapter as claimed in claim 1 wherein said body further includes at least one latch adapted to engage the bottom end of a vial disposed within said inner cavity for retaining the vial within said inner cavity.

4. The vial adapter as claimed in claim 3 wherein said latch is an L-shaped member having a radially-extending arm and a longitudinally extending arm.

5. The vial adapter as claimed in claim 1 wherein said hollow piercing member comprises a tubular shaft having a top end and a bottom end, an enlarged head disposed at said bottom end of said tubular shaft and at least one opening in at least one of said tubular shaft and said enlarged head for accessing the interior of said tubular shaft.

6. The vial adapter as claimed in claim 5 wherein said enlarged head has a flat top end and a pointed bottom end.

7. The vial adapter as claimed in claim 6 wherein said enlarged head is substantially two-sided.

8. The vial adapter as claimed in claim 1 further comprising a tubular member having a top portion and a bottom portion, said bottom portion being in fluid communication with said tubular shaft of said hollow piercing member.

9. The vial adapter as claimed in claim 8 wherein said top portion of said tubular member comprises a female luer.

10. The vial adapter as claimed in claim 8 wherein said top portion of said tubular member comprises a female luer lock.

11. The vial adapter as claimed in claim 8 further comprising means for controlling fluid flow from said bottom portion of said tubular member to said top portion of said tubular member.

12. The vial adapter as claimed in claim 11 wherein said means for controlling fluid flow comprises a valve disposed within said tubular member, said valve being movable, upon insertion of a deflecting member into said top portion of said tubular member, from a first position in which said valve blocks fluid flow from said bottom portion of said tubular member to said top portion of said tubular member to a second position in which said valve does not block fluid flow from said bottom portion of said tubular member to said top portion of said tubular member.

13. The vial adapter as claimed in claim 11 wherein said valve is a resiliently flexible member.

14. The vial adapter as claimed in claim 1 wherein said body comprises a sleeve and a jacket, said sleeve having a bottom end, said jacket being overmolded onto said bottom end of said sleeve.

15. The vial adapter as claimed in claim 1 wherein said bottom end of said body is generally square and wherein each of the four sides of said bottom end of said body has a concave surface.

16. The vial adaptor as claimed in claim 1, further comprising a plurality of longitudinally extending ribs for limiting the upward insertion into said inner cavity of a vial whose septum is covered by a cap, said plurality of longitudinally extending ribs being formed along the inside surface of said body.

17. A vial adapter for use in transferring fluid from a vial, the vial having a top end and a bottom end, the top end of the vial being sealed with a septum, said vial adapter comprising:

(a) a body, said body having a top end, a bottom end and an inner cavity, being dimensioned to receive the vial, with the bottom end of said body extending below the bottom end of the vial, said body further including a sleeve and a jacket, said sleeve having a bottom end, said jacket being overmolded onto said bottom end of said sleeve, said jacket having a bottom end, said bottom end being generally polygonal, each of the sides of said bottom end having a concave surface;

(b) a needle-bearing member mounted within said body, said needle-bearing member comprising a hollow needle extending downwardly into said inner cavity of said body for puncturing the septum of a vial disposed in said inner cavity;

(c) a luer-lock-bearing member mounted on said top end of said body, said luer-lock-bearing member comprising a top portion and a bottom portion separated by a radial wall, said top portion being a female luer-lock, said bottom portion including a tubular member in fluid communication with said hollow needle; and (d) a valve disposed within said luer-lock-bearing member for controlling fluid flow from said bottom portion of said luer-lock-bearing member to said top portion of said luer-lock-bearing member.

18. The vial adapter as claimed in claim 17 wherein said sleeve includes an annular top wall, a circular side wall, a skirt and an open bottom.

19. The vial adapter as claimed in claim 18 wherein said circular side wall is interiorly shaped to include a plurality of longitudinally extending ribs for limiting the upward insertion into said inner cavity of a vial whose septum is covered by a cap.

20. The vial adapter as claimed in claim 17 wherein said jacket is interiorly shaped to include a plurality of latches for retaining a vial within said body, each of said latches being a resiliently flexible L-shaped member including a radially-extending arm and a longitudinally-extending arm.

21. The vial adapter as claimed in claim 17 wherein said hollow needle comprises a tubular shaft, an enlarged head and at least one opening providing fluid access to the interior of said tubular shaft, said enlarged head deterring removal of said hollow needle from a vial whose septum has been punctured therewith.

22. The vial adapter as claimed in claim 21 wherein said needle-bearing member further comprises a top portion and an intermediate portion, said top portion and said intermediate portion together defining a cavity having an open top end, said hollow needle extending downwardly from said intermediate portion and being in fluid communication with said cavity.

23. The vial adapter as claimed in claim 22 wherein said valve has a bottom end and wherein said intermediate portion comprises a plurality of valve supports upon which said bottom end of said valve is seated.

24. The vial adapter as claimed in claim 23 wherein said top portion of said needle-bearing member is received in and secured to said bottom portion of said luer-lock-bearing member.

25. The vial adapter as claimed in claim 17 wherein said body and said needle-bearing member having complementary means for deterring rotational movement of said needle-bearing member relative to said body.

26. The vial adapter as claimed in claim 17 wherein said body and said luer-lock-bearing member having complementary means for deterring rotational movement of said luer-lock-bearing member relative to said body.

27. The vial adapter as claimed in claim 17 wherein said valve is a resiliently flexible member movable, upon insertion of a male luer tip into said tubular member of said luer-lock-bearing member, from a first position in which said valve blocks fluid flow from said bottom portion of said tubular member to said top portion of said tubular member to a second position in which said valve does not block fluid flow from said bottom portion of said tubular member to said top portion of said tubular member.

28. The vial adaptor as claimed in claim 17, wherein said bottom end is generally square and wherein each of the four sides of said bottom end has a concave surface.

* * * * *